United States Patent
Lee et al.

(10) Patent No.: US 9,566,035 B2
(45) Date of Patent: Feb. 14, 2017

(54) X-RAY DETECTOR AND METHOD OF MANUFACTURING THE SAME

(71) Applicant: Samsung Electronics Co., Ltd., Suwon-si, Gyeonggi-do (KR)

(72) Inventors: Changbum Lee, Seoul (KR); Sunil Kim, Osan-si (KR); Dongwook Lee, Suwon-si (KR); Jaechul Park, Yangju-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/704,529

(22) Filed: May 5, 2015

(65) Prior Publication Data

US 2016/0100812 A1    Apr. 14, 2016

(30) Foreign Application Priority Data

Oct. 14, 2014  (KR) .................. 10-2014-0138615

(51) Int. Cl.

| | |
|---|---|
| *G01T 1/24* | (2006.01) |
| *A61B 6/00* | (2006.01) |
| *G01T 1/17* | (2006.01) |
| *G01T 7/00* | (2006.01) |
| *A61B 6/04* | (2006.01) |

(52) U.S. Cl.
CPC .......... *A61B 6/4233* (2013.01); *A61B 6/0407* (2013.01); *A61B 6/502* (2013.01); *G01T 1/17* (2013.01); *G01T 7/00* (2013.01)

(58) Field of Classification Search
CPC ........................................... G01T 1/24
See application file for complete search history.

(56) References Cited

U.S. PATENT DOCUMENTS

| 5,886,353 | A | * | 3/1999 | Spivey et al. ........... 250/370.09 |
|---|---|---|---|---|
| 7,507,512 | B2 | | 3/2009 | Yanoff et al. |
| 8,970,916 | B2 | | 3/2015 | Nakamura |
| 2010/0230607 | A1 | * | 9/2010 | Kitada .................... 250/370.08 |
| 2012/0181440 | A1 | * | 7/2012 | Kim et al. ............... 250/370.01 |
| 2014/0034836 | A1 | * | 2/2014 | Takei et al. .................. 250/366 |

FOREIGN PATENT DOCUMENTS

| JP | 11-121916 | 4/1999 |
|---|---|---|
| JP | H11121916 A | 4/1999 |
| JP | 4702499 | 6/2011 |
| JP | 4702499 B1 | 6/2011 |
| JP | 2011-194885 | 10/2011 |
| JP | 2011194885 A | 10/2011 |
| JP | 2012156924 | 8/2012 |
| JP | 2013-161871 | 8/2013 |
| JP | 2013161871 A | 8/2013 |

* cited by examiner

*Primary Examiner* — David Porta
*Assistant Examiner* — Hugh H Maupin

(57) ABSTRACT

A method of manufacturing an X-ray detector includes: applying a mask having an opening on a substrate on which a plurality of charge detection units are positioned; filling the opening with a paste including a photoelectric conversion material that absorbs X-rays to generate charges; and forming a photoconductive layer from the paste by separating the mask from the substrate. A thickness of the paste within the opening is thicker in an area adjacent to at least one edge among edges of the opening than in areas around other edges.

20 Claims, 8 Drawing Sheets

X-RAY DETECTOR AND METHOD OF MANUFACTURING THE SAME

RELATED APPLICATION

This application claims the benefit of Korean Patent Application No. 10-2014-0138615, filed on Oct. 14, 2014, in the Korean Intellectual Property Office, the disclosure of which is incorporated herein in its entirety by reference.

BACKGROUND

1. Field

Example embodiments relate to X-ray detectors and/or methods of manufacturing the same.

2. Description of the Related Art

X-rays are used in various fields for industrial, scientific, or healthcare purposes. For example, X-rays are used for non-destructive inspection, material structure and physical property inspection, image diagnosis, and security checks. An X-ray imaging system, such as an X-ray apparatus, includes an X-ray generator that emits X-rays and an X-ray detector that detects X-rays passing through a subject.

In an analog X-ray apparatus, a film plate, which is a combination of a silver salt film and a screen (fluorescent plate) responsive to X-rays, is employed as an X-ray detector. The film plate is replaced whenever inspection is performed. Recently, a digital X-ray apparatus employing a digital X-ray detector has been introduced. Such a digital X-ray apparatus includes in comparison to the analog X-ray apparatus a signal processor that generates a captured image based on a detection signal of a digital X-ray detector.

The digital X-ray detector includes a photoconductive layer that is responsive to X-rays to generate electrons and holes, and a charge detection unit that detects the generated electrons or holes. The quality of a captured image may depend on the degree of uniformity of the photoelectric conversion characteristic of the photoconductive layer. For example, the uniformity of the thickness of the photoconductive layer may greatly affect the quality of the captured image.

SUMMARY

Example embodiments relate to methods of manufacturing an X-ray detector including a uniform photoconductive layer and/or X-ray detectors having a reduced dead zone around a chest wall, and methods of manufacturing the same.

Additional aspects will be set forth in part in the description which follows and, in part, will be apparent from the description, or may be learned by practice of the presented example embodiments.

According to an aspect of an example embodiment, an X-ray detector includes: an X-ray detection unit including a photoconductive layer configured to receive X-rays and generate charges, a substrate on which a plurality of charge detection units are arranged to detect the generated charges, and an electrode positioned on the photoconductive layer; and a case that accommodates the X-ray detection unit, wherein a distance between a chest wall of the case and an edge adjacent to the chest wall may be 2 mm or less.

A connection portion may be provided on the substrate and be electrically connected to the charge detection unit, and the connection portion may be positioned around edges of the case except for the chest wall thereof.

A thickness of the photoconductive layer may be in the range of about 100 µm to about 200 µm.

The charge detection unit may include a thin film transistor.

According to an aspect of another example embodiment, a method of manufacturing an X-ray detector includes: (a) putting a mask having an opening on a substrate on which a plurality of charge detection units are positioned; (b) filling the opening with a paste including a photoelectric conversion material that absorbs X-rays to generate charges; and (c) forming a photoconductive layer from the paste by separating the mask from the substrate. A thickness of the paste filled in the opening in the operation (b) may be thicker in an area adjacent to at least one edge among edges of the opening than areas around other edges.

The operation (b) may be performed by screen printing.

The operation (b) may include filling the opening with the paste remaining on the mask while moving a squeegee so that a squeegeeing portion of the squeegee comes into contact with the mask, and the squeegeeing portion may include a first portion corresponding to a central area of the opening and a second portion positioned on at least one side of the first portion in a length direction of the squeegeeing portion and stepped concavely from the first portion.

The second portion may be parallel to the first portion.

The second portion may have an oblique line shape.

The second portion may have a curved shape.

A stepped amount of the second portion with respect to the first portion may be smaller than a thickness of the opening.

The second portion may extend inwardly from the edge of the opening about 0.5 mm or more.

BRIEF DESCRIPTION OF THE DRAWINGS

These and/or other aspects will become apparent and more readily appreciated from the following description of the example embodiments, taken in conjunction with the accompanying drawings in which.

DETAILED DESCRIPTION

Figure 1:
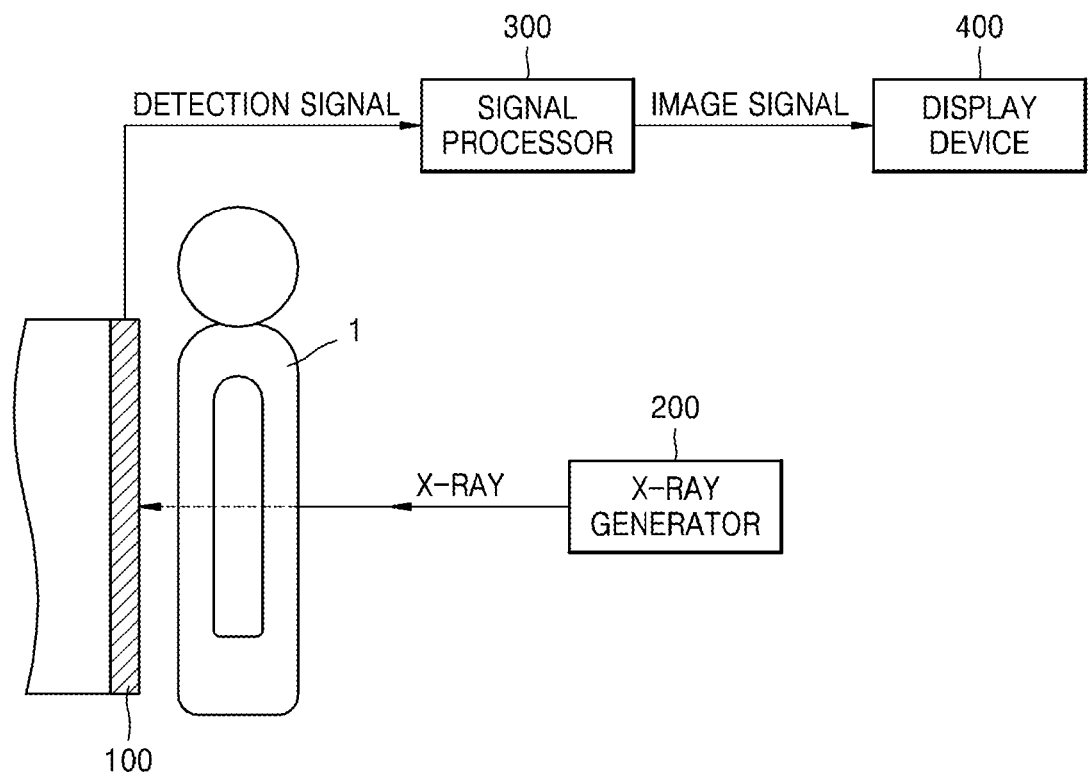
FIG. 1 is a configuration diagram of an X-ray apparatus according to an example embodiment.

Reference will now be made in detail to example embodiments, some examples of which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the figures, to explain aspects.

Example embodiments will now be described more fully with reference to the accompanying drawings, in which some example embodiments are shown. In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

FIG. 1 is a configuration diagram of an X-ray apparatus according to an example embodiment.

Referring to FIG. 1, an X-ray apparatus may acquire an internal image of a subject by transmitting X-rays through the subject. The X-ray apparatus is capable of acquiring the internal image of a subject in a convenient manner within a short time as compared to an imaging apparatus such as a magnetic resonance imaging (MRI) apparatus or a computerized tomography (CT) apparatus. Therefore, the X-ray apparatus may be used to acquire a medical image of a human body through a chest tomography, an abdominal tomography, a skeletal structure tomography, or a breast tomography.

The X-ray apparatus may include an X-ray generator 200, an X-ray detector 100, and a signal processor 300. The X-ray apparatus may further include a display device 400 that displays a captured image. The X-rays emitted from the X-ray generator 200 pass through a subject 1 and are incident on the X-ray detector 100. The X-ray detector 100 detects the X-rays passing through the subject 1 and transmits a detection signal to the signal processor 300. The signal processor 300 generates an image signal from the detection signal through image processing, and the display device 400 displays the image signal in a visible image form. Since the configuration of the signal processor 300 and the process of generating the image signal from the detection signal are well known to those skilled in the art, a detailed description thereof will be omitted. In addition to the configuration of FIG. 1, the X-ray apparatus may further include an input unit that allows a user to input a capturing condition setting, for example, a capturing area setting, an X-ray intensity setting, or an X-ray radiation time setting.

Figure 2:
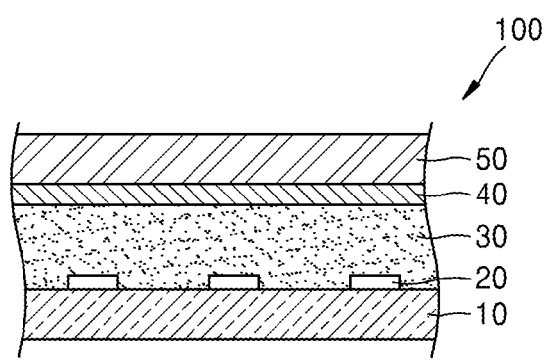
FIG. 2 is a cross-sectional diagram of an X-ray detector according to an example embodiment.
Figure 3:
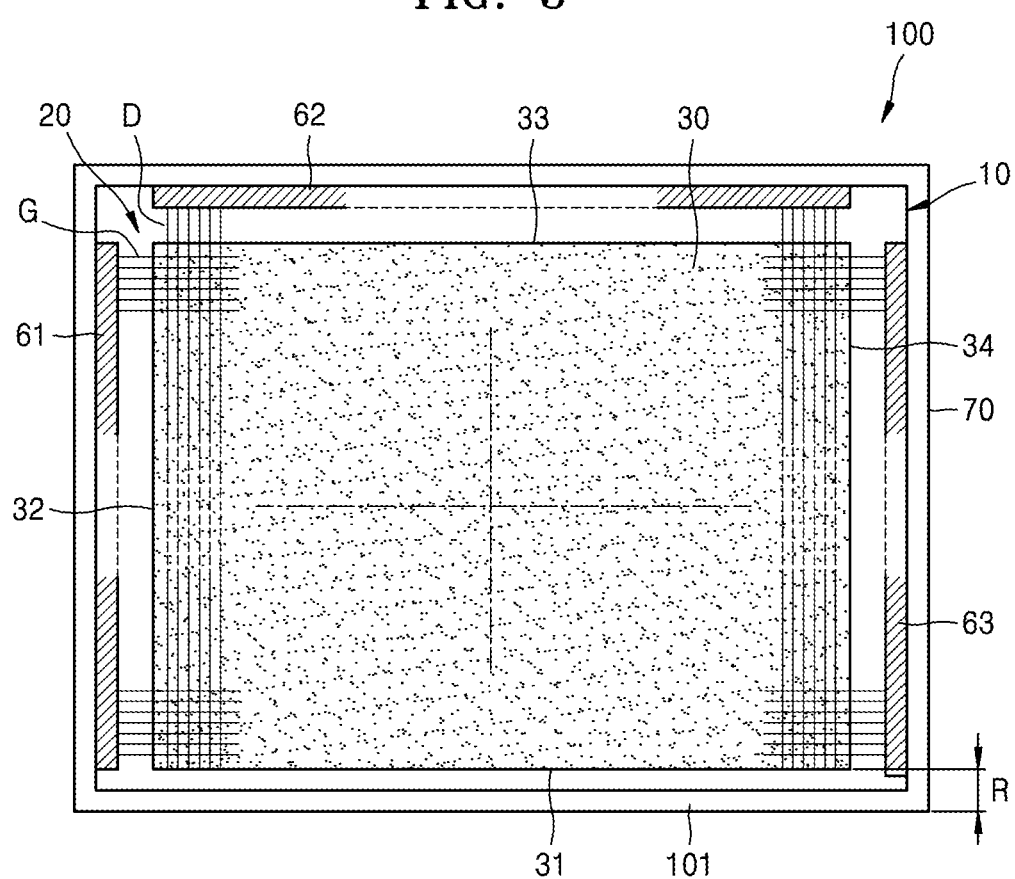
FIG. 3 is a cross-sectional diagram of the X-ray detector of FIG. 2.
Figure 4:
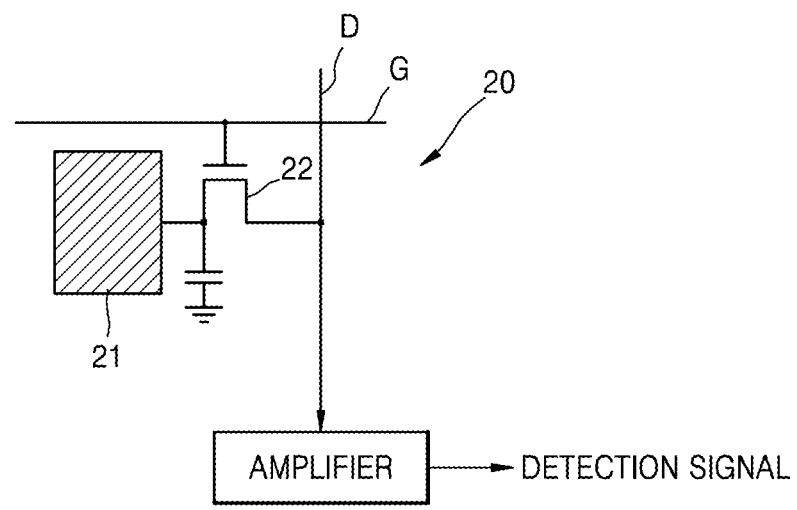
FIG. 4 is a configuration diagram of a charge detection unit according to an example embodiment.

FIG. 2 is a cross-sectional diagram of the X-ray detector 100 according to an example embodiment. FIG. 3 is a plan view of the X-ray detector 100 of FIG. 2, according to an example embodiment. FIG. 4 is a configuration diagram of a charge detection unit 20 according to an example embodiment.

Referring to FIGS. 2 and 3, the X-ray detector 100 may include an X-ray detection unit that detects X-rays, and a case (housing) 70 that accommodates the X-ray detection unit. The X-ray detection unit may include a substrate 10 on which a plurality of charge detection units 20 are arranged, a photoconductive layer 30, and an electrode 40. A protective film 50 may be disposed on the electrode 40.

The charge detection unit 20 and the photoconductive layer 30 of the x-ray detector 100 are illustrated in plan view of FIG. 3, while the electrode 40 and the protective film 50 are not illustrated in the plan view of FIG. 3.

The photoconductive layer 30 is a material layer including a photoelectric conversion material that absorbs X-rays and generates charges, for example, electrons and holes. For example, the photoconductive layer 30 may be a material layer including at least one of lead iodide ($PbI_2$), lead monoxide (PbO), lead dioxide ($PbO_2$), cadmium telluride (CdTe), cadmium zinc telluride (CdZnTe), bismuth triiodide ($BiI_3$), and mercury iodide ($HgI_2$).

In some example embodiments, mercury iodide ($HgI_2$) is used as the photoconductive material constituting the photoconductive layer 30. For example, the photoconductive layer 30 may have a thickness of about 100 μm to about 200 μmm.

The charge detection unit 20 may detect charges, that is, electrons or holes, which are generated in the photoconductive layer 30 by the X-rays. For example, when a negative voltage is applied to the electrode 40, the charge detection unit 20 detects electrons, and vice versa. That is, when a positive voltage is applied to the electrode 40, the charge detection unit 20 detects holes.

The charge detection unit 20 may include a thin film transistor (TFT) array. Referring to FIGS. 3 and 4, thin film transistors 22 are disposed at intersecting positions of gate lines G and data lines D arranged in a two-dimensional matrix form. A single thin film transistor 22 forms a single pixel. For example, when electrons and holes are generated in the photoconductive layer 30 by X-rays and a negative voltage is applied to the electrode 40, the electrons are collected at a charge collector electrode 21. When the gate line D is activated, a current flows from the charge collector electrode 21 to the data line D. A current signal flowing through the data line D, for example, may be amplified by an amplifier and be output as a detection signal. The signal processor 300 may convert the detection signal into an image signal through a series of image processing processes, such as analog-to-digital conversion, noise cancellation, and the like.

Referring again to FIG. 3, connection portions (connectors) 61, 62, and 63, which are electrically connected to the charge detection unit 20, may be provided on the substrate 10. A driving signal for driving the charge detection unit 20 and the detection signal output from the charge detection unit 20 may be transmitted or received through the connection portions 61, 62, and 63.

The connection portions 61, 62, and 63 may be connected to a circuit element (not illustrated) that transmits or receives the driving signal and the detection signal. For example, in a case where the thin film transistor 22 is used as the charge detection unit 20, the gate line G and the data line D may be connected to the circuit element through the connection portions 61, 62, and 63. The circuit element may include a driving circuit element (not illustrated) that is provided in the connection portions 61 and 63 to supply the driving signal for driving the thin film transistor 22 through the gate line G, and a detection circuit element (not illustrated) (for example, an amplifier) that is provided in the connection portion 62 to receive the detection signal (current signal) flowing through the charge collector electrode 21 and the data line D. For example, circuit elements may be connected to the connection portions 61, 62, and 63 by chip on flexible printed circuit (COF) bonding.

Figure 5A:
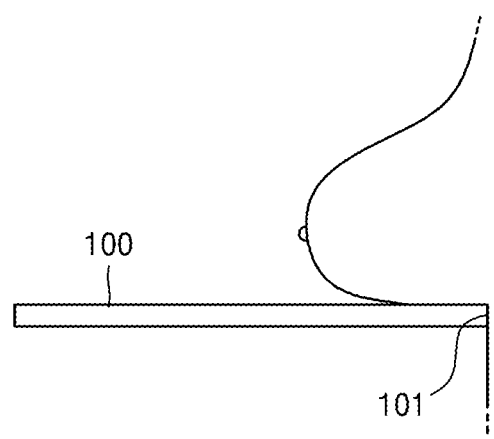
FIGS. 5A and 5B are a side view and a plan view, respectively, illustrating a case where the X-ray detector captures a breast.
Figure 5B:
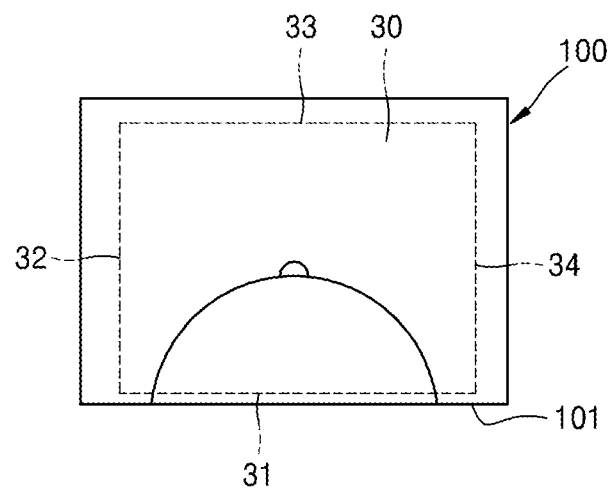

FIGS. 5A and 5B are a side view and a plan view, respectively, illustrating a case where the X-ray detector 100 captures a breast.

Referring to FIGS. 5A and 5B, at the time of capturing a breast, one edge 101 of the X-ray detector 100 is brought into close contact with the human body. The edge 101 of the X-ray detector 100 is referred to as a chest wall 101.

In order for accurately capturing the breast, an effective detection area of the X-ray detector 100 may need to approach the chest wall 101 as close as possible.

Referring to FIG. 5B, the effective detection area of the X-ray detector 100 may be determined by the photoconductive layer 30. Therefore, it may be desirable that an edge 31 of the photoconductive layer 30 adjacent to the chest wall 101 is closer to the chest wall 101. The remaining edges 32, 33, and 34 of the photoconductive layer 30 that are not adjacent to the chest wall 101 may not affect capturing even when the edges 32, 33, and 34 are slightly spaced apart from the corresponding edges of the X-ray detector 100.

Therefore, referring to FIG. 3, it is desirable to reduce a distance between the chest wall 101 and the edge 31 of the photoconductive layer 30 adjacent to the chest wall 101. When the distance is set to about 2 mm or less in consideration of the thickness of the case 70 of the X-ray detector 100, the accuracy of the breast diagnosis may be improved.

As illustrated in FIGS. 3 and 5B, to achieve such a small distance between the chest wall 101 and the edge 31 of the photoconductive layer 30, no connection portion may be provided between the edge 31 of the photoconductive layer 30 and the chest wall 101 thereof. Therefore, the connection portions 61, 62, and 63 may be provided along edges of the case 70 except for the chest wall 101 thereof. That is, the connection portions 61, 62, and 63 may be provided between the edges 32, 33, and 34 of the photoconductive layer 30 except for the edge 31 thereof, and edges of the case 70 except for the chest wall 101 thereof.

In an area adjacent to the chest wall 101, the thickness of the photoconductive layer 30 may need to be uniform up to the edge 31 thereof so as to obtain a high quality image. For example, the photoconductive layer 30 may be formed by coating a paste containing a photoelectric conversion material on the substrate 10 by screen printing and then curing the paste.

Figure 6A:
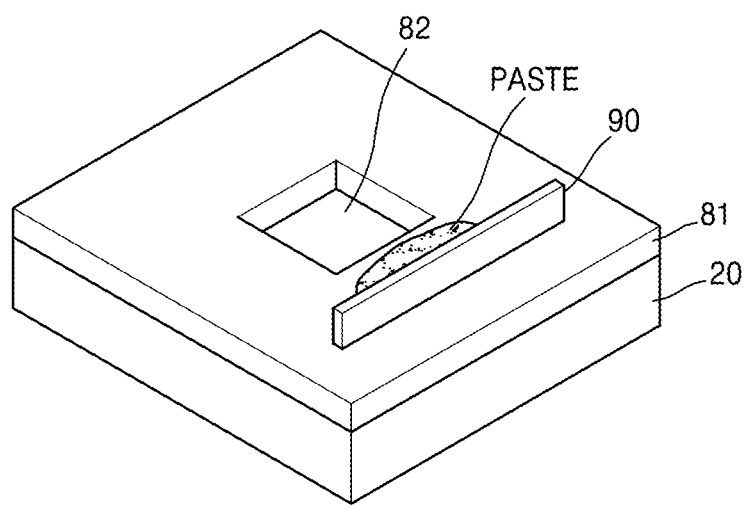
FIGS. 6A to 6C are diagrams illustrating a process of forming a photoconductive layer by screen printing, as an example of a method of manufacturing an X-ray detector.
Figure 6B:
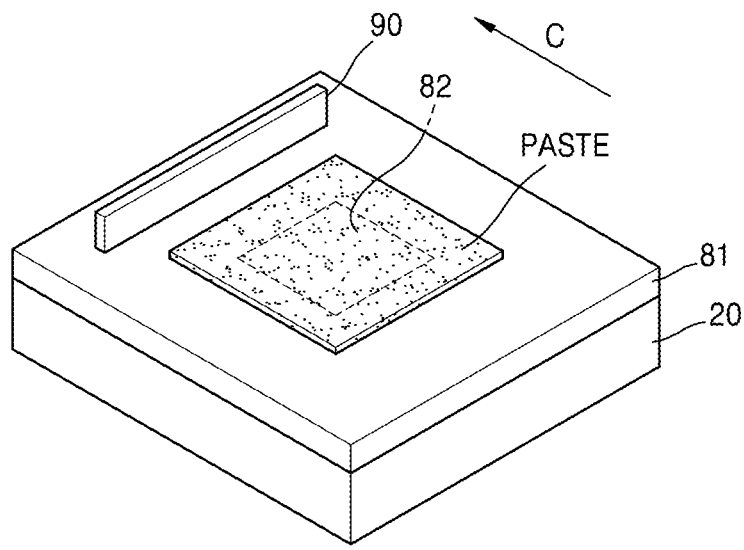
Figure 6C:
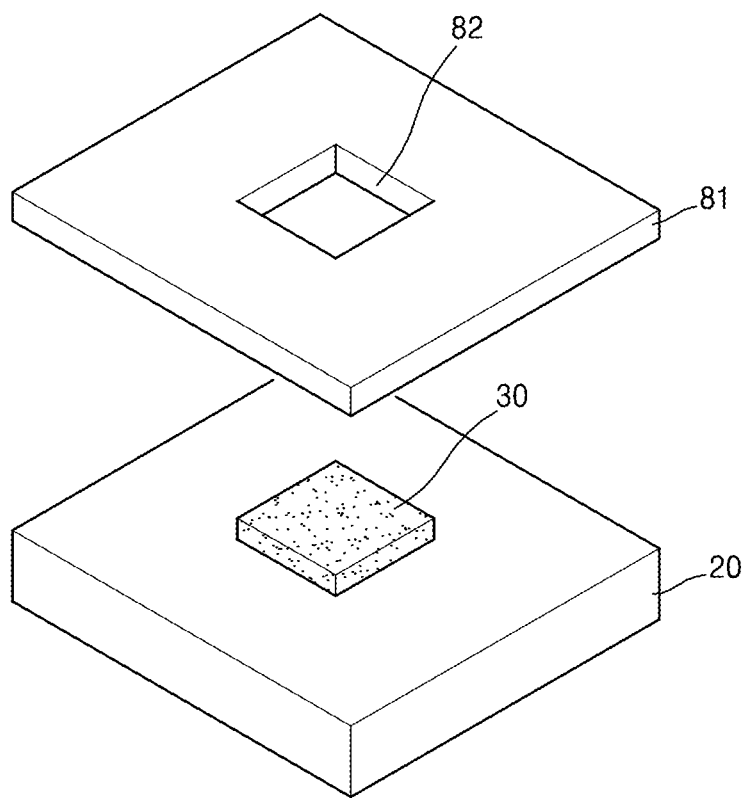

FIGS. 6A to 6C are diagrams illustrating a process of forming the photoconductive layer 30 by screen printing, as an example of the method of manufacturing the X-ray detector 100.

Referring to FIG. 6A, a mask 81 is formed to have an opening 82 defining an area in which a photoconductive layer 30 is to be formed, and the mask 81 is positioned on the charge detection units 20 and the substrate 10. A paste PASTE containing a photoelectric conversion material, for example, mercury iodide, is put on the mask 81. A viscosity of the paste may be in the range of about 100,000 cps to about 150,000 cps.

Then, as illustrated in FIG. 6B, screen printing is performed using a squeegee 90. That is, the squeegee 90 is moved in a direction of an arrow C so that the paste runs thinly and pushes into the opening 82. In this way, the opening 82 is filled with the paste.

Then, as illustrated in FIG. 6C, when the mask 81 is separated from the substrate 10, the photoconductive layer 30 having the same shape as the opening 82 is formed on the charge detection units 20 and the substrate 10.

Although not illustrated, after the process of FIG. 6C, a process of curing the paste, a process of forming the electrode 40, a process of forming the protective film 50, and a process of accommodating a resulting structure in the case 70 may be further performed.

As described above, the paste has a very high viscosity and thus has a strong adhesion. Therefore, when the mask 81 is separated from the substrate 10 in operation of FIG. 6C, the paste may be attached to the edge of the opening 82.

Figure 7:
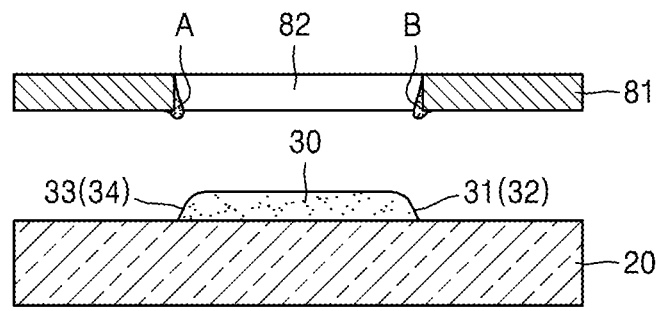
FIG. 7 is a diagram illustrating a process of separating a mask from a substrate after screen printing.

FIG. 7 is a diagram illustrating a process of separating the mask 81 from the substrate 10 after the screen printing.

Referring to FIG. 7, high-viscosity pastes A and B may be attached to the edges of the opening 82, and the pastes A and B attached to the edges of the opening 82 may be separated from the substrate 10 together with the mask 81. Thus, conventionally, the thickness of the photoconductive layer 30 may be non-uniform as a whole. For example, the thickness of the edges 31 to 34 may be thinner than that of the central area.

Figure 8:
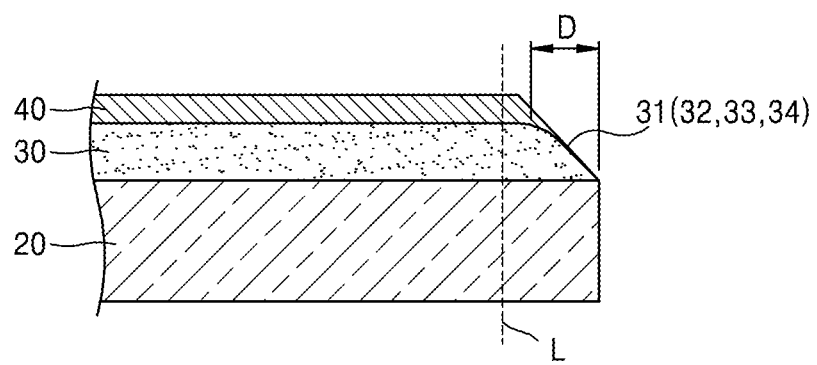
FIG. 8 is a partial cross-sectional view illustrating a case where an electrode is formed in a photoconductive layer of FIG. 7.

FIG. 8 is a partial cross-sectional view illustrating a case where the electrode 40 is formed in the photoconductive layer 30 of FIG. 7.

Referring to FIG. 8, conventionally, an edge area D of the photoconductive layer 30 may be thinner than a central area thereof. Therefore, the difference in thickness between the central area and the edge area D may affect the quality of the captured image. For example, when the same amount (or intensity) of the X-rays is incident, an amount of charges generated is smaller in the edge area D than in the central area. Consequently, the edge area D may be a dead zone that cannot secure the quality of the image.

As discussed above, in the case of the breast tomography, it may be necessary to acquire an accurate image up to an interface between a breast and a trunk or chest wall 101. Therefore, in one or more example embodiments, a dead zone is reduced by forming a sufficiently thick photoconductive layer 30 up to the edge area D of the chest wall 101.

A method of cutting the edge area D along a cutting-plane line in FIG. 8 may be considered. However, in this case, since the cutting-plane line L is very close to the charge detection unit 20 formed on the substrate 10, that is, the thin film transistor array, the charge detection unit 20 adjacent to the cutting-plane line L may be damaged during the cutting process, and an additional process is required, thus increasing a manufacturing cost of the X-ray detector 100.

In contrast, in one or more example embodiments, the photoconductive layer 30 is produced to have a sufficient thickness in the edge area D by screen printing, without additional processes.

As discussed in more detail below, according to some example embodiments, the paste in the opening 82 formed by operation of FIG. 6B may be thicker in an area adjacent to at least one edge among the edges than in the other areas. Accordingly, even when some of the paste around the edge of the opening 82 is separated from the charge detection units 20 and the substrate 10 along with the mask 81, it is possible to maintain the paste around the edge of the opening 82 at a desired thickness.

Figure 9:
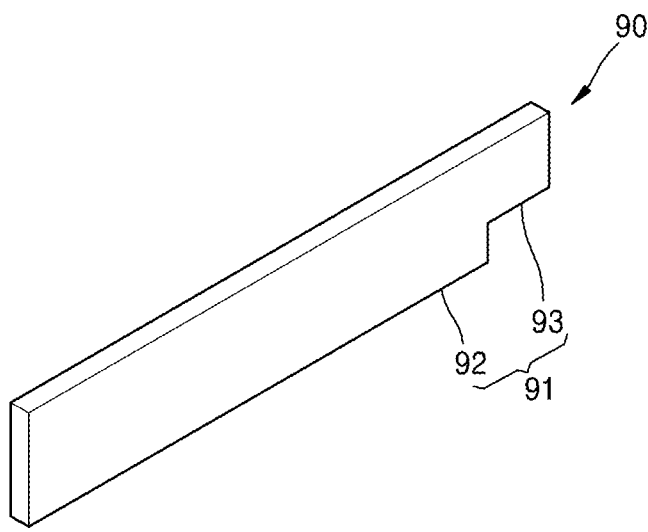
FIG. 9 is a side view of a screen printing squeegee for obtaining a photoconductive layer of a sufficient thickness.

FIG. 9 is a side view of the screen printing squeegee 90 for obtaining the photoconductive layer 30 having a sufficient thickness up to the edge area D.

Referring to FIG. 9, the squeegee 90 includes a squeegeeing portion 91 that makes a paste run thinly on the mask 81. At the time of the screen printing, the squeegee 90 moves in a direction C so that the squeegeeing portion 91 comes into contact with the top surface of the mask 81. In this way, the paste on the mask 81 runs thinly and fills the opening 82.

At the time of the screen printing, the squeegee 90 has a length in a direction perpendicular to the moving direction C of the squeegee 90. The squeegeeing portion 91 includes a first portion 92 corresponding to the central area of the opening 82, and a second portion 93 positioned on at least one side of the first portion 92 in a length direction and stepped concavely from the first portion 92. The squeegee 90 may be made of acryl or a rubber.

Figure 10:
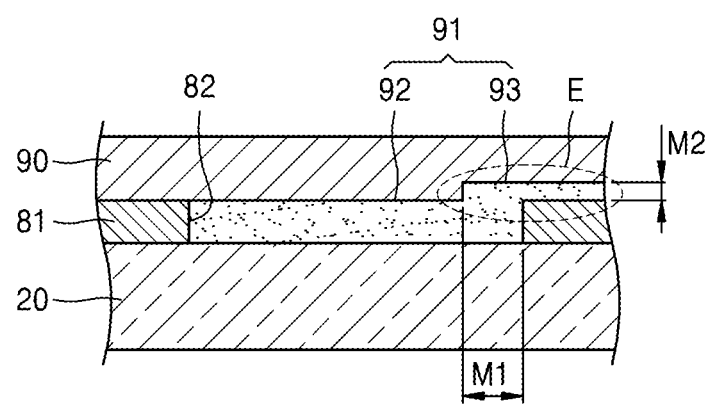
FIG. 10 is a cross-sectional view illustrating a case where screen printing is performed using the squeegee of FIG. 9.
Figure 11:
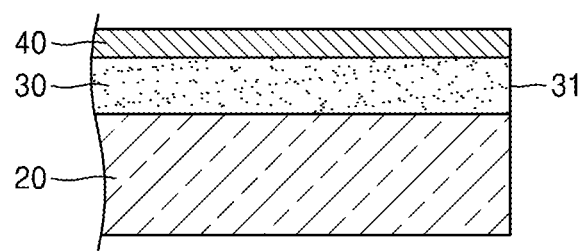
FIG. 11 is a partial cross-sectional view illustrating a case where an electrode is formed in a photoconductive layer after the screen printing of FIG. 10.

FIG. 10 is a cross-sectional view illustrating a case where screen printing is performed using the squeegee 90 of FIG. 9. FIG. 11 is a partial cross-sectional view illustrating a case where the electrode 40 is formed in the photoconductive layer 30 after the screen printing of FIG. 10.

Referring to FIG. 10, as indicated by reference symbol "E", the edge area of the opening 82, that is, the edge 31 of the photoconductive layer 30, after the screen printing is formed thicker than the other areas due to the second portion 93 that is concave with respect to the first portion 92.

When separating the mask 81, the paste is coated on a part of the mask 81 as indicated by reference symbols A and B of FIG. 7. However, as discussed above, squeegee 90 applies the paste such that the photoelectric conversion material is thicker in the edge 31. Thus, even when the mask 81 is separated from the substrate 10, the edge 31 of the photoconductive layer 30 may be maintained at a desired thickness as illustrated in FIG. 11.

The second portion 93 may be provided at a position corresponding to the edge 31 of the photoconductive layer 30 adjacent to the chest wall 101. In order to set a distance R between the chest wall 101 and the edge 31 of the photoconductive layer 30 adjacent to the chest wall 101 to about 2 mm or less in consideration of the thickness of the case 70, for example, about 1.5 mm, the non-effective area may be defined as an area up to about 0.4 mm inwardly from the edge of the opening 82. Therefore, the second portion 93 may extend inwardly from the edge of the opening 82 about 0.4 mm or more, and may extend inwardly from the edge of the opening 82 about 0.5 mm or more, including a process margin.

That is, in FIG. 10, M1 may be about 0.5 mm or more. Therefore, by limiting the range of the non-effective area between the chest wall 101 and the edge 31 of the photoconductive layer 30 adjacent to the chest wall 101 to about 0.5 mm or less, the distance R (see FIG. 3) between the chest wall 101 and the edge 31 of the photoconductive layer 30 adjacent to the chest wall 101 may be set to about 2 mm or less.

In addition, a stepped amount M2 of the second portion 93 with respect to the first portion 92 may be determined considering the thickness of the paste that is separated together when the mask 81 is separated. For example, since the paste around the edge of the opening 82 is not completely lost, the stepped amount of the second portion 93 with respect to the first portion 92 may be smaller than the thickness of the photoconductive layer 30, that is, the thickness of the opening 82. The stepped amount M2 may be appropriately determined within a range of less than 100% of the thickness of the opening 82, considering the viscosity of the paste, the size of the opening 82, or the like.

Due to the above-described configuration, it is possible to secure a desired thickness even around the edge 31 of the photoconductive layer adjacent to the chest wall 101, thus reducing the dead zone around the chest wall 101. Therefore, it is possible to secure the image quality at the time of the breast tomography and it is possible to more accurately diagnose the presence or absence of lesion. In addition, it is possible to minimize the dead zone without additional processes such as cutting in the manufacturing process, thus reducing manufacturing costs. It is possible to reduce a risk of damage to the charge detection unit 20 due to the cutting, thus improving the yield of the X-ray detector.

Regarding FIG. 9, the squeegee 90 in which the first portion 92 and the second portion 93 are parallel to each other has been described, but example embodiments are not limited thereto.

Figure 12:
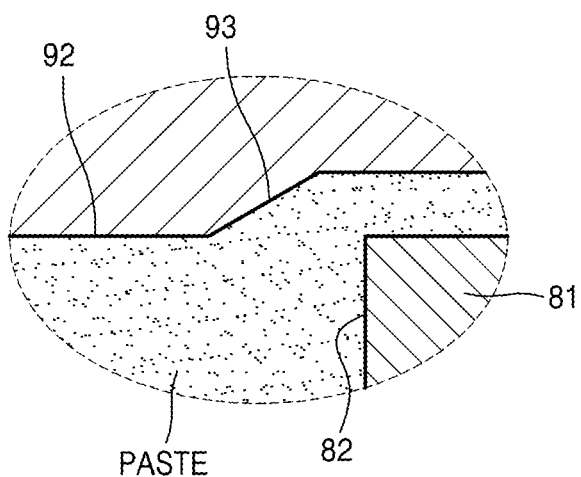
FIGS. 12 and 13 are views of squeegees according to example embodiments.
Figure 13:
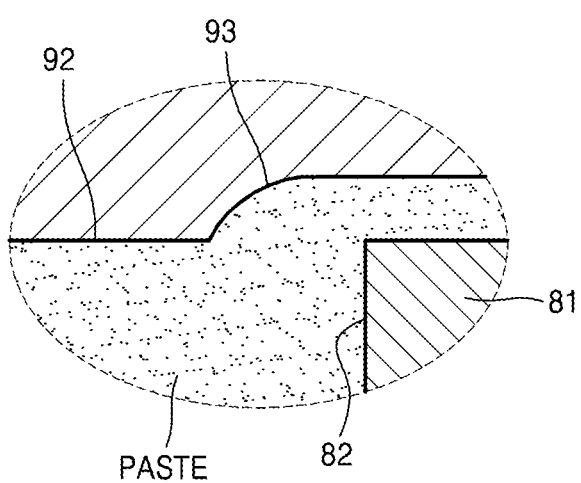

FIGS. 12 and 13 are views of squeegees according to example embodiments.

For example, as illustrated in FIG. 12, the second portion 93 of the squeegee 90 may be formed to have an oblique line extending diagonally (e.g., on a slant) from the first portion 92.

In addition, as illustrated in FIG. 13, the second portion 93 may be formed to have a curved shape extending from the first portion 92. Furthermore, the second portion 93 may have various shapes capable of compensating an amount of a paste that is lost when the mask 81 is separated.

Moreover, the second portion 93 is illustrated in FIG. 9 as being provided at one side of the first portion 92 in a length direction, but the second portion 93 may be provided at both sides of the first portion 92.

It should be understood that the example embodiments described therein should be considered in a descriptive sense only and not for purposes of limitation. Descriptions of features or aspects within each exemplary embodiment should typically be considered as available for other similar features or aspects in other exemplary embodiments.

While one or more example embodiments have been described with reference to the figures, it will be understood by those of ordinary skill in the art that various changes in form and details may be made therein without departing from the spirit and scope as defined by the following claims.

What is claimed is:

1. An X-ray detector comprising:
   an X-ray detection unit including a photoconductive layer configured to receive X-rays and generate charges, a plurality of charge detection units on a substrate, the plurality of charge detection units configured to detect the generated charges, and an electrode on the photoconductive layer; and
   a housing including a chest wall configured to butt against a trunk of a patient, the housing configured to accommodate the X-ray detection unit such that a distance between the chest wall and an edge of the photoconductive layer adjacent to the chest wall is 2 mm or less.

2. The X-ray detector of claim 1, further comprising:
   connectors on the substrate corresponding to edges of the housing except for the chest wall, the connectors configured to transmit one or more of a driving signal to the charge detection unit and a detection signal from the charge detection unit.

3. The X-ray detector of claim 1, wherein a thickness of the photoconductive layer is between 100 µm and 200 µm.

4. The X-ray detector of claim 1, wherein the charge detection unit includes a thin film transistor.

5. A method of manufacturing an X-ray detector, comprising:
   applying a mask on a substrate such that the mask has a plurality of edges that define an opening therein, the substrate having a plurality of charge detection units positioned thereon;
   filling the opening with a paste such that a thickness of the paste filled in the opening is thicker in at least one of the edges than in other ones of the edges and in a central area of the opening, the paste including a photoelectric conversion material configured to absorb X-rays to generate charges; and
   forming a photoconductive layer from the paste by separating the mask from the substrate.

6. The method of claim 5, wherein the filling is performed by screen printing.

7. The method of claim 6, wherein
   the filling includes moving a squeegee in a moving direction so that the paste on the mask is thinly dispersed and fills the opening so that a squeegeeing portion of the squeegee comes in to contact with the mask, and
   the squeegeeing portion includes a first portion and at least one second portion, the first portion corresponding to the central area of the opening and the at least one second portion positioned on at least one side of the first portion in a length direction of the squeegeeing portion, that is perpendicular to the moving direction of the squeegee, and stepped concavely a stepped amount from the first portion.

8. The method of claim 7, wherein the second portion is parallel to the first portion.

9. The method of claim 7, wherein the second portion has an oblique line shape.

10. The method of claim 7, wherein the second portion has a curved shape.

11. The method of claim 7, wherein the stepped amount is smaller than a thickness of the opening.

12. The method of claim 7, wherein the second portion extends at least 0.5 mm inwardly from the at least one of the edges of the opening.

13. An X-ray apparatus comprising:
   an X-ray generator configured to emit X-rays; and
   an X-ray detector comprising:
      an X-ray detection unit including:
         a photoconductive layer configured to receive the X-rays and generate charges,
         a plurality of charge detection units on a substrate, the plurality of charge detection units configured to detect the generated charges, and
         an electrode on the photoconductive layer; and
      a housing comprising a chest wall configured to contact a torso of a patient, the housing configured to enclose the X-ray detection unit, wherein the housing is dimensioned such that a distance between the chest wall and an edge of the photoconductive layer adjacent to the chest wall is 2 mm or less.

14. The X-ray apparatus of claim 13, further comprising:
   connectors on the substrate corresponding to edges of the housing except for the chest wall, the connectors configured to transmit one or more of a driving signal to the charge detection unit and a detection signal from the charge detection unit.

15. The X-ray apparatus of claim 13, wherein a thickness of the photoconductive layer is between 100 µm and 200 µm.

16. The X-ray apparatus of claim 13, wherein the charge detection unit includes a thin film transistor.

17. The X-ray apparatus of claim 13, the X-ray detection unit further comprising a protective film disposed on the electrode.

18. The X-ray apparatus of claim 13, further comprising a signal processor configured to generate an image signal from a detection signal generated by the X-ray detection unit through image processing.

19. The X-ray apparatus of claim 18, further comprising a display configured to receive the image signal and display a captured image.

20. The X-ray apparatus of claim 18, further comprising an input unit configured to enable a user to input a capturing condition setting.

* * * * *